United States Patent
Depui et al.

[19]

[11] Patent Number: 6,136,344
[45] Date of Patent: *Oct. 24, 2000

[54] ORAL PHARMACEUTICAL DOSAGE FORM

[75] Inventors: Helene Depui, Göteborg; Adam Rosinski, Mölndal, both of Sweden

[73] Assignee: Astra Aktiebolag, Sodertalje, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/628,712

[22] PCT Filed: Feb. 2, 1996

[86] PCT No.: PCT/SE96/00125

§ 371 Date: Apr. 15, 1996

§ 102(e) Date: Apr. 15, 1996

[87] PCT Pub. No.: WO96/24375

PCT Pub. Date: Aug. 15, 1996

Related U.S. Application Data

[63] Continuation-in-part of application No. 08/464,775, Jun. 7, 1995, abandoned.

[30] Foreign Application Priority Data

Feb. 6, 1995 [SE] Sweden ................................. 9500422

[51] Int. Cl.$^7$ .............................. A61K 9/26; A61K 31/33
[52] U.S. Cl. ...................... 424/470; 424/464; 424/468; 424/469
[58] Field of Search ..................................... 424/451, 457, 424/458, 459, 462, 464, 468, 475, 482, 469, 470; 514/300

[56] References Cited

U.S. PATENT DOCUMENTS

| | | |
|---|---|---|
| 4,786,505 | 11/1988 | Lovgren et al. .................... 424/468 |
| 4,853,230 | 8/1989 | Lövgren ................................. 424/466 |
| 5,196,205 | 3/1993 | Borody ..................................... 424/653 |
| 5,476,669 | 12/1995 | Borody ..................................... 424/653 |
| 5,599,794 | 2/1997 | Eek et al. . | |
| 5,629,305 | 5/1997 | Eek et al. . | |
| 5,753,265 | 5/1998 | Bergstrand et al. ...................... 424/474 |
| 5,817,338 | 10/1998 | Bergstrand et al. ...................... 424/468 |

FOREIGN PATENT DOCUMENTS

| | | |
|---|---|---|
| 0005129 | 4/1979 | European Pat. Off. . |
| 0008780 | 8/1979 | European Pat. Off. . |
| 0072021 | 8/1982 | European Pat. Off. . |
| 0080341 | 11/1982 | European Pat. Off. . |

(List continued on next page.)

OTHER PUBLICATIONS

J. R. Warren, The Lancet, Jun. 4, 1983, p. 1273.

Dialog Information Services, File 73, EMBASE, Dialog accession No. 9150953, EMBASE accession No. 94095444, Logan R.P.H. et al: "Eradication of Helicobacter pylori with clarithromycin and omeprazole", GUT (United Kingdom), 1994, 35/3 (323–326).

*Primary Examiner*—Gollamudi S. Kishore
*Attorney, Agent, or Firm*—White & Case LLP

[57] ABSTRACT

An oral pharmaceutical dosage form comprising an acid susceptible proton pump inhibitor and one or more antibacterial compounds in a fixed formulation. The fixed formulation is intended for oral use and in the form of an enteric coating layered tablet, an capsule or a multiple unit tableted dosage form. The multiple unit dosage form is most preferred. The new fixed formulation is especially useful in the treatment of disorders associated with Helicobacter infections.

25 Claims, 1 Drawing Sheet

FOREIGN PATENT DOCUMENTS

| | | |
|---|---|---|
| 0108295 | 10/1983 | European Pat. Off. . |
| 0108504 | 10/1983 | European Pat. Off. . |
| 0111103 | 10/1983 | European Pat. Off. . |
| 0170752 | 12/1984 | European Pat. Off. . |
| 0166287 | 6/1985 | European Pat. Off. . |
| 0174726 | 7/1985 | European Pat. Off. . |
| 0013566 | 1/1990 | European Pat. Off. . |
| 0391518 | 2/1990 | European Pat. Off. . |
| 0365947 | 5/1990 | European Pat. Off. . |
| 0541369 | 11/1992 | European Pat. Off. . |
| 0587220 | 8/1993 | European Pat. Off. . |
| 0648487 | 10/1994 | European Pat. Off. . |
| 0642797 | 3/1995 | European Pat. Off. . |
| 2066070 | 12/1980 | United Kingdom . |
| 2091097 | 11/1981 | United Kingdom . |
| 2132887 | 11/1983 | United Kingdom . |
| 2163747 | 8/1985 | United Kingdom . |
| 2285989 | 1/1995 | United Kingdom . |
| 8501207 | 9/1984 | WIPO . |
| 8503436 | 2/1985 | WIPO . |
| 8702240 | 9/1986 | WIPO . |
| 8903219 | 4/1989 | WIPO . |
| 9006925 | 12/1989 | WIPO . |
| 9119711 | 6/1991 | WIPO . |
| 9119712 | 12/1991 | WIPO . |
| 9203135 | 3/1992 | WIPO . |
| 9211849 | 7/1992 | WIPO . |
| 9312772 | 12/1992 | WIPO . |
| 9403160 | 7/1993 | WIPO . |
| 9321920 | 11/1993 | WIPO . |
| 9427988 | 5/1994 | WIPO . |
| 9501972 | 7/1994 | WIPO . |
| 9510264 | 4/1995 | WIPO . |
| 9601623 | 1/1996 | WIPO . |

_

ORAL PHARMACEUTICAL DOSAGE FORM

This application is a 371 of PCT/SE96/00125 filed Feb. 2, 1996 and a continuation-in-part of application Ser. No. 08/464,775, filed on Jun. 7, 1995, now abandoned.

FIELD OF THE INVENTION

The present invention is related to new oral pharmaceutical preparations especially for use in the treatment of disorders associated with Helicobacter infections. The present preparations comprise an acid susceptible proton pump inhibitor in combination with one or more antibacterial compounds in a new fixed unit dosage form, especially a tableted dosage form. Furthermore, the present invention refers to a method for the manufacture of such preparations and the use of such preparations in medicine, especially in the treatment of Helicobacterpylori infections.

BACKGROUND OF THE INVENTION

The relationship between gastrointestinal disorders and infections with *Helicobacter pylori* proposed in 1983 by Warren (Warren J R Lancet 1983;1.1273) is well established today. A number of different therapies have been proposed for treatment of *H. pylori* infections. Most of these therapies comprise different combinations of antibacterial compounds. Some of these therapies also comprise a bismuth compound, see for instance WO 89/03219 (Borody). Other combination therapies comprise a proton pump inhibitor and one or more antibacterial compounds, for instance a combined regimen of omeprazole and amoxicillin which has been approved by regulatory authorities in for example Great Britain and Sweden for the treatment of *H. pylori* infections. Different triple therapies, for example omeprazole, clarithromycin and amoxicillin or other antibacterial substances, have recently been reported at the 10th World Congresses of Gastroenterology in October 1994. Some published patent applications in this field are for instance:

WO 93/00327, Astra Aktiebolag, which discloses the combination of a substance with inhibiting effect on the gastric acid secretion which increases the intragastric pH and an acid degradable antibacterial compound. The proposed combination is especially suitable for the treatment of *H. pylori* infections.

WO 92/03135, Smithkline & French Laboratories, which discloses a combination of a benzimidazole and an anti-Helicobacter agent, i.e. for instance pantoprazole in combination with amoxicillin and/or metronidazole.

In these proposed combination therapies each single active substance is administred separately in different dosage forms, each one comprising only one single active substance. It is well known that patient compliance is a main factor in receiving a good result in medical treatments, especially in the treatment of *H. pylori* infections. Administration of two, three or even more different tablets to the patient is not convenient or satisfactory to achieve the most optimal results. The present invention now provides new oral dosage forms comprising two or more different active substances combined in one fixed unit dosage form, preferably a tablet.

It is well known that proton pump inhibitors are susceptible to degradation/transformation in acid reacting and neutral media. In respect of the stability properties, it is obvious that one of the active substances being a proton pump inhibitor must be protected from contact with acidic gastric juice by an enteric coating layer. There are different enteric coating layered preparations of omeprazole as well as other proton pump inhibitors described in the prior art, see for example U.S. Pat. No. 4,786,505 (A B Hässle).

There are problems to produce a fixed unit dosage form comprising a rather high amount of active substances. Different active substances in the same preparation give further problems. Preparation of a multiple unit tableted dosage form raises specific problems when enteric coating layered pellets containing acid susceptible proton pump inhibitors as active substance are compressed into tablets. If the enteric coating layer does not withstand the compression of the pellets into a tablet the susceptible active substance will be destroyed upon administration by penetrating acidic gastric juice, i.e. the acid resistance of the enteric coating layer of the pellets will not be sufficient in the tablet after compression.

SUMMARY OF THE INVENTION

The present invention provides oral, fixed unit dosage forms, i.e. multiple unit tableted dosage forms, enteric coating layered tablets, multilayered tablets or a capsule filled with more than one pharmaceutically active compound. The active compounds present are preferably an acid susceptible proton pump inhibitor and one or more antibacterial substances. These new dosage forms will simplify the regimen and improve the patient compliance.

DETAILED DESCRIPTION OF THE INVENTION

One object of the invention is to provide an oral, multiple unit tableted dosage form comprising an acid susceptible proton pump inhibitor in the form of individually enteric coating layered units together with one or more antibacterial compounds in the form of a powder or granules compressed into a tablet. The enteric coating layer(s) covering the individual units of the acid susceptible proton pump inhibitor has properties such that the compression of the units into a tablet does not significantly affect the acid resistance of the individually enteric coating layered units. Furthermore, the multiple unit tableted dosage form provides a good stability during long-term storage to the active substances. Alternatively, the prepared tablet has separate layers, one layer is in the form of compressed enteric coated layered units comprising the proton pump inhibitor and another layer comprises the antibacterial compound(s).

Figures 1, 2:
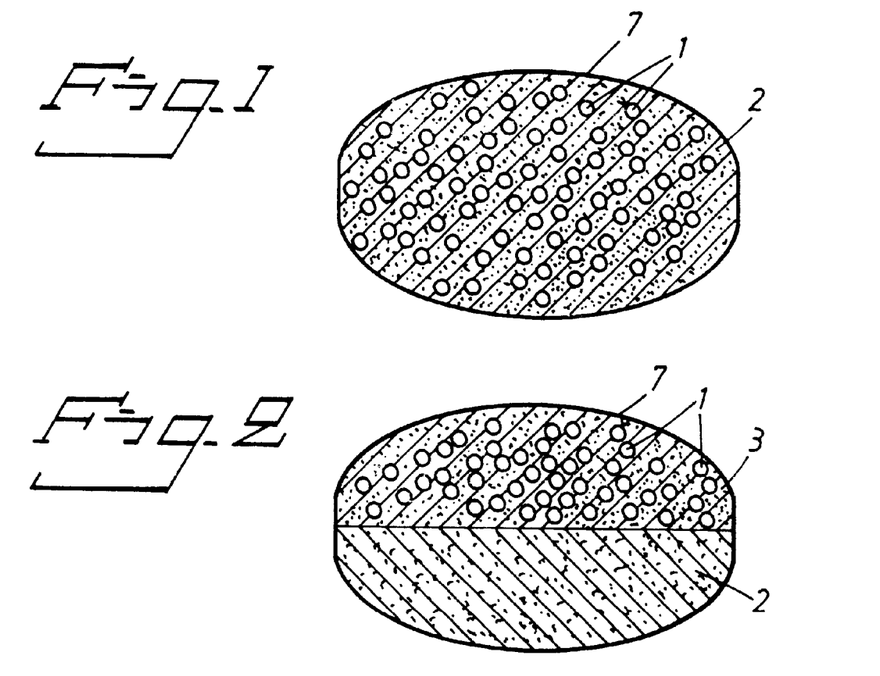
FIG. 1 illustrates a cross-section of a multiple unit tableted dosage form comprising an acid susceptible proton pump inhibitor in the form of enteric coating layered pellets (1) in admixture with an antibacterial granulation (2). The tablet is covered by an overcoating layer (7).
FIG. 2 illustrates a cross-section of a tablet with two separate layers, one layer comprises enteric coating layered pellets of an acid susceptible proton pump inhibitor (1) in admixture with excipients (3) and the other layer comprises the antibacterial compound(s) (2). The tablet is covered by an overcoating layer (7).
Figure 3:
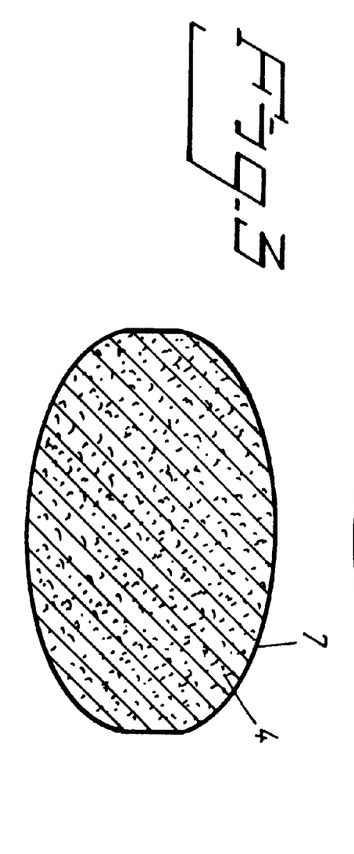
FIG. 3 illustrates a cross-section of an enteric coating layered tablet comprising an acid susceptible proton pump inhibitor in admixture with one or more antibacterial substances (4). The tablet is covered by an enteric coating layer (7).
Figure 4:
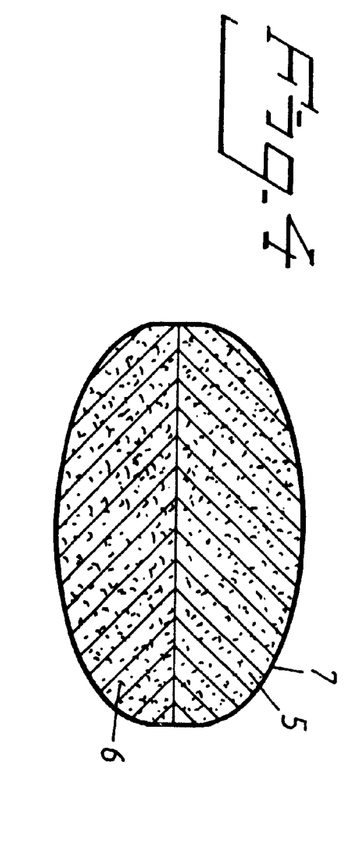
FIG. 4 illustrates an enteric coating layered tablet consisting of two separate layers, one layer comprises an acid susceptible proton pump inhibitor (5) and the other layer comprises the antibacterial compound(s) (6).

The new fixed dosage form is preferably in the form of a multiple unit tableted dosage form comprising enteric coating layered units of the one of the active substance which is acid susceptible, i.e. the proton pump inhibitor, and granules of the other active substance(s), i.e. the antibacterial granulation, as shown in FIGS. 1 and 2. Alternatively, the different active compounds may be intimately mixed with each other and compressed into a conventional tablet, which is enteric coated as shown in FIGS. 3 and 4. As a further alternative, the different active substances are dry mixed and filled into a capsule. In the latter preparation the acid susceptible proton pump inhibitor is in the form of enteric coating layered units (1).

Another object of the invention is to provide a tablet preparation comprising an acid susceptible proton pump inhibitor in admixture with one or more antibacterial substances compressed into a tablet, which tablet is enteric coating layered. Optionally a separating layer is applied before the tablet is enteric coating layered. Alternatively, the prepared tablet core has separate layers, each one comprising different active substances. One of the layers comprises the acid susceptible proton pump inhibitor and another layer(s) comprises(-e) the antibacterial substance or substances, respectively. The prepared tablet is thereafter enteric coating layered.

A further object of the invention is to provide a dosage form which is divisible, such as divisible tablets.

Still a further object of the invention is to provide a multiple unit tableted dosage form, which is divisible and easy to handle. The multiple unit tableted dosage form may be dispersed in an aqueous liquid and can be given to patients with swallowing disorders and in pediatrics. Such a suspension of dispersed units/pellets of appropriate size can be used for oral administration and also for feeding through a naso-gastric tube.

Furthermore, the present invention provides a capsule preparation comprising the acid susceptible proton pump inhibitor in the form of enteric coating layered pellets mixed with one or more antibacterial compounds in the form of granules or pellets.

The antibacterial components may be formulated in the form of instant release, sustained release or extended release formulations. Alternatively, the components may be formulated in an effervescent formulation.

The new fixed unit dosage forms comprise as active substances an acid susceptible proton pump inhibitor and one or more antibacterial compounds. The different active components used in the dosage forms are defined below.

Active Substances

The proton pump inhibitors are for example compounds of the general formula I

I wherein

Het$_1$ is

Het$_2$ is

X = wherein

N in the benzimidazole moiety means that one of the carbon atomns substituted by R$_6$–R$_9$ optionally may be exchanged for a nitrogen atom without any substituents;

R$_1$, R$_2$ and R$_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

R$_4$ and R$_5$ are the same or different and selected from hydrogen, alkyl and aralkyl;

R$_6$' is hydrogen, halogen, trifluoromethyl, alkyl and alkoxy;

R$_6$–R$_9$ are the same or different and selected from hydrogen, alkyl, alkoxy, halogen, haloalkoxy, alkylcarbonyl, alkoxycarbonyl, oxazolyl, trifluoroalkyl, or adjacent groups R$_6$–R$_9$ form ring structures which may be further substituted;

R$_{10}$ is hydrogen or forms an alkylene chain together with R$_3$ and

R$_{11}$ and R$_{12}$ are the same or different and selected from hydrogen, halogen or alkyl and alkyl groups, alkoxy groups and moities thereof may be branched and straight C$_1$–C$_9$-chains or comprise cyclic alkyl groups, for example cycloalkylalkyl.

Examples of proton pump inhibitors according to formula I are

Omeprazole

Lansoprazole

Pantoprazole

Pariprazole

Leminoprazole

The proton pump inhibitors used in the dosage forms of the invention may be used in neutral form or in the form of an alkaline salt, such as for instance the $Mg^{2+}$, $Ca^{2+}$, $Na^+$, $K^+$ or $Li^+$ salts, preferably the $Mg^{2+}$ salts. Further where applicable, the compounds listed above may be used in racemic form or in the form of a substantially pure enantiomer thereof, or alkaline salts of the single enantiomers.

Suitable proton pump inhibitors are for example disclosed in EP-A1-0005129, EP-A1-174 726, EP-A1-166 287, GB 2 163 747 and WO90/06925, WO91/19711, WO91/19712, and further especially suitable compounds are described in WO95/01977 and WO94/27988.

A wide variety of antibacterial compounds may be used in combination with a suitable proton pump inhibitor in the fixed unit dosage form according to the present invention. Such antibacterial compounds include for example nitroiridazole antibiotics, tetracyclines, penicillins, cephalosporins, carbopenems, aminoglycosides, macrolide antibiotics, lincosamide antibiotics, 4-quinolones, rifamycins and nitrofurantoin. In the following examples of such antibacterial compounds are listed: ampicillin, amoxicillin, benzylpenicillin, phenoxymethylpenicllllin, bacampicillin, pivampicillln, carbenicillin, cloxacillin, cyclacillin, dicloxacillin, methicillin, oxacillin, piperacillin, ticarcillin, flucloxacillin, cefuroxime, cefetamet, cefetrame, cefixime, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycin, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol. The active antibacterial agents could be in standard forms or used as salts, hydrates, esters etc. A combination of two or more of the above listed drugs may be used, for example to minimize the risk for developing resistance. Preferable antibacterial compounds for the new fixed dosage form are clarithromycin, erythromycin, roxithromycin, azithromycin, amoxicillin, metronidazole, tinidazole and tetracycline. Clarithromycin and metronidazole alone or in combination are especially suitable.

The preferred multiple unit tableted dosage form comprising a proton pump inhibitor in the form of a racemat, an alkaline salt or one of its single enantiomers and one or more antibacterial compounds, is characterized in the following way. Individually enteric coating layered units (small beads, granules or pellets) containing the acid susceptible proton pump inhibitor and optionally containing alkaline reacting substances, are mixed with the antibacterial compound(s) and conventional tablet excipients. Preferably, the antibacterial compound(s) and tablet excipients are in the form of a granulation. The dry mixture of enteric coating layered units, antibacterial granulation and optionally excipients are compressed into the multiple unit tableted dosage forms. With the expression "individual units" is meant small beads, granules or pellets, in the following referred to as pellets of the proton pump inhibitor.

The compaction process (compression) for formulating the multiple unit tableted dosage form must not significantly affect the acid resistance of the enteric coating layered pellets. In other words the mechanical properties, such as the flexibility and hardness as well as the thickness of the enteric coating layer(s), must secure that the requirements on enteric coated articles in the United States Pharmacopeia are accomplished in that the acid resistance does not decrease more than 10% during the compression of the pellets into tablets.

The acid resistance is defined as the amount of proton pump inhibitor in the tablets or pellets after being exposed to simulated gastric fluid USP, or to 0.1 M HCl (aq) relative to that of unexposed tablets and pellets, respectively. The test is accomplished in the following way. Individual tablets or pellets are exposed to simulated gastric fluid of a temperature of 37° C. The tablets disintegrate rapidly and release the enteric coating layered pellets to the medium. After two hours the enteric coating layered pellets are removed and analyzed for content of the proton pump inhibitor using High Performance Liquid Chromatography (HPLC).

Further specific components used in the fixed unit dosage forms of the present invention are defined below.

Core Material—for Enteric Coating Layered Pellets Comprising a Proton Pump Inhibitor The core material for the individually enteric coating layered pellets can be constituted according to different principles. Seeds layered with the acid susceptible proton pump inhibitor, optionally mixed with alkaline substances, can be used as the core material for the further processing.

The seeds which are to be layered with the acid susceptible proton pump inhibitor can be water insoluble seeds comprising different oxides, celluloses, organic polymers and other materials, alone or in mixtures or water-soluble seeds comprising different inorganic salts, sugars, nonpareils and other materials, alone or in mixtures. Further, the seeds may comprise the proton pump inhibitor in the form of crystals, agglomerates, compacts etc. The size of the seeds is not essential for the present invention but may vary between approximately 0.1 and 2 mm. The seeds layered with the proton pump inhibitor are produced either by powder or solution/suspension layering using for instance granulation or spray coating layering equipment.

Before the seeds are layered, the proton pump inhibitor may be mixed with further components. Such components can be binders, surfactants, fillers, disintegrating agents, alkaline additives or other and/or pharmaceutically acceptable ingredients alone or in mixtures. The binders are for example are celluloses such as hydroxypropyl methylcellulose (HPMC), hydroxypropyl-cellulose (HPC), carboxymethylcellulose sodium, polyvinyl pyrrolidone (PVP), sugar or starch or other pharmaceutically acceptable substances with cohesive properties. Suitable surfactants are found in the groups of pharmaceutically acceptable non-ionic or ionic surfactants such as for instance sodium lauryl sulfate.

Alternatively, the proton pump inhibitor optionally mixed with alkaline substances and further mixed with suitable constituents can be formulated into core material. Said core material may be produced by extrusion/spheronization, balling or compression utilizing conventional process equipment. The size of the formulated core material is approximately between 0.1 and 4 mm and preferably between 0.1 and 2 mm. The manufactured core material can further be layered with additional ingredients comprising the proton pump inhibitor and/or be used for further processing.

The proton pump inhibitor is mixed with pharmaceutical constituents to obtain preferred handling and processing properties and a suitable concentration of the substance in the final mixture. Pharmaceutical constituents such as fillers, binders, lubricants, disintegrating agents, surfactants and other pharmaceutically acceptable additives.

Further, the proton pump inhibitor may also be mixed with an alkaline, pharmaceutically acceptable substance (or substances). Such substances can be chosen among, but are not restricted to substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16}CO_3.4H_2O)$, $MgO.Al_2O_3.2SiO_2.nH_2O$ or similar compounds; organic pH-buffering substances such as trihydroxymethylaminomethane, basic amino acids and their salts or other similar, pharmaceutically acceptable pH-buffering substances.

Alternatively, the aforementioned core material can be prepared by using spray drying or spray congealing technique.

Enteric Coating Layer(s)

Before applying the enteric coating layer(s) onto the core material in the form of individual pellets, the pellets may optionally be covered with one or more separating layer(s) comprising pharmaceutical excipients optionally including alkaline compounds such as pH-buffering compounds. This/these separating layer(s), separate(s) the core material from the outer layers being enteric coating layer(s).

The separating layer(s) can be applied to the core material by coating or layering procedures in suitable equipments such as coating pan, coating granulator or in a fluidized bed apparatus using water and/or organic solvents for the coating process. As an alternative the separating layer(s) can be applied to the core material by using powder coating technique. The materials for the separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium, water soluble salts of enteric coating polymers and others, used alone or in mixtures. Additives such as plasticizers, colorants, pigments, fillers anti-tacking and anti-static agents, such as for instance magnesium stearate, titanium dioxide, talc and other additives may also be included into the separating layer(s).

When the optional separating layer, is applied to the core material it may constitute a variable thickness. The maximum thickness of the separating layer(s) is normally only limited by processing conditions. The separating layer may serve as a diffusion barrier and may act as a pH-buffering zone. The pH-buffering properties of the separating layer(s) can be further strengthened by introducing into the layer(s) substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgO.CO_2.12H_2O$, $(Mg_6Al_2(OH)_{16}CO_3.4H_2O)$, $MgO.Al_2O_3.2SiO_2.nH_2O$, aluminium bicarbonate coprecipitate or similar compounds; or other pharmaceutically acceptable pH-buffering compounds such as, for instance the sodium, potassium, calcium, magnesium and aluminium salts of phosphoric, carbonic, citric or other suitable, weak, inorganic or organic acids; or suitable organic bases, including basic amino acids and salts thereof. Talc or other compounds may be added to increase the thickness of the layer(s) and thereby strenghten the diffusion barrier. The optionally applied separating layer(s) is not essential for the invention. However, the separating layer(s) may improve the chemical stability of the active substance and/or the physical properties of the novel multiple unit tableted dosage form.

Alternatively, the separating layer may be formed in situ by a reaction between an enteric coating polymer layer applied on the core material and an alkaline reacting compound in the core material. Thus, the separating layer formed comprises a water soluble salt formed between the enteric coating layer polymer(s) and an alkaline reacting compound which is in the position to form a salt.

One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers one or more, separately or in combination, of the following can be used, e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s).

The enteric coating layers contain pharmaceutically acceptable plasticizers to obtain the desired mechanical properties, such as flexibility and hardness of the enteric coating layers. Such plasticizers are for instance, but not restricted to triacetin, citric acid esters, phthalic acid esters, dibutyl sebacate, cetyl alcohol polyethylene glycols, polysorbates or other plasticizers.

The amount of plasticizer is optimized for each enteric coating layer formula, in relation to selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that the acid resistance of the pellets covered with enteric coating layer(s) does not decrease significantly during compression of pellets into tablets. The amount of plasticizer is usually above 10% by weight of the enteric coating layer polymer(s), preferably 15–50% and more preferably 20–50%. Additives such as dispersants, colorants, pigments polymers e.g. poly (ethylacrylat, methylmethacrylat), anti-tacking and anti-foaming agents may also be included into the enteric coating layer(s). Other compounds may be added to increase film thickness and to decrease diffusion of acidic gastric juices into the acid susceptible material.

To protect the acid susceptible substance, the proton pump inhibitor, and to obtain an acceptable acid resistance of the dosage form according to the invention, the enteric coating layer(s) constitutes a thickness of approximately at least 10 $\mu$m, preferably more than 20 $\mu$m. The maximum thickness of the applied enteric coating is normally only limited by processing conditions.

Alternatively the enteric coating layer described above may be used for enteric coating layering of conventional tablets comprising a composition of an acid susceptible proton pump inhibitor and one or more antibacterial compounds, optionally covered by one of the separating layers described above. As a further alternative, the proton pump inhibitor may be replaced in such a tablet by another gastric acid suppressing agents, such as a $H_2$-receptor antagonist, for instance ranitidine, cimetidine or famotidine.

Over-Coating Layer

Pellets covered with enteric coating layer(s) may further be covered with one or more over-coating layer(s). The over-coating layer(s) can be applied to the enteric coating layered pellets by coating or layering procedures in suitable equipments such as coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such for instance magnesium stearate, titanium dioxide, talc and other additives may also be included into the over-coating layer(s). Said over-coating layer may further prevent potential agglomeration of enteric coating layered pellets, further it may protect the enteric coating layer towards cracking during the compaction process and enhance the tableting process. The maximum thickness of the applied over-coating layer(s) is normally only limited by processing conditions.

The above described over-coating layer may also be used as a tablet coating layer to obtain tablets of good appearance.

Antibacterial Granulation

The active substance in the form of one or more antibacterial compounds is dry mixed with inactive excipients and the mixture is wet massed with a granulation liquid. The wet mass is dried preferably to a loss on drying of less than 3% by weight. Thereafter the dry mass is milled to a suitable size for the granules, such as smaller than 4 mm, and preferably smaller than 1 mm. Suitable inactive excipients for the antibacterial granulation are for instance, sodium starch glycolate, corn starch, crosslinked polyvinyl pyrrolidone, low substituted hydroxypropyl cellulose, microcrystalline cellulose and colloidal silicon dioxide anhydrous (Aerosil®). The dry mixture comprising antibacterial compound(s) is mixed with a suitable granulation liquid comprising for instance, polyvinyl pyrrolidone, hydroxypropyl cellulose, and optionally wetting agents, such as sodium lauryl sulphate, dissolved in purified water. Suitable lubricants for the tableting process are for instance, sodium stearyl fumarate, magnesium stearate and talc.

Multiple Unit Tablets

The enteric coating layered pellets comprising a proton pump inhibitor are mixed with the granules comprising antibacterial compounds and tablet excipients. The dry mixture is compressed into a multiple unit tableted dosage form The compressed tablet is optionally covered with a film-forming agent(s) to obtain a smooth surface of the tablet and further enhance the stability of the tablet during packaging and transport. Such a tablet coating layer may further comprise additives such as anti-tacking agents, colorants and pigments or other additives to obtain a tablet of good appearance.

The enteric coated pellets with or without an over-coat and the antibacterial granulation are mixed with tablet excipients such as fillers, binders, disintegrants, lubricants and other pharmaceutically acceptable additives and compressed into tablets.

The amount of enteric coating layered pellets constitutes less than 75% by weight of the total tablet weight and preferably less than 60%. By choosing small enteric coating layered pellets in the formulation according to the present invention, the number of pellets in each tablet can be held heigh which in turn makes the tablet divisible with retained dosing accuracy. Larger amount of the granulation comprising the antibacterial compound(s) may reduce the amount of enteric coating layered pellets in the multiple unit tableted dosage form.

Thus, the preferred multiple unit tablet formulation consists of enteric coating layered pellets containing one active substance in the form of an acid susceptible proton pump inhibitor, optionally mixed with alkaline reacting compound (s), compressed into tablet together with a granulation containing antibacterial compound(s) and optionally tablet excipients. The addition of an alkaline reacting material to the proton pump inhibitor is not necessary, in any sense but such a substance may further enhance the stability of the proton pump inhibitor or some of the alkaline reacting compounds may react in situ with the enteric coating material to form a separating layer. The enteric coating layer(s) is making the pellets of the dosage form insoluble in acidic media, but disintegrating/dissolving in near neutral to alkaline media such as, for instance the liquids present in the proximal part of the small intestine, where dissolution of the proton pump inhibitor is desired. The antibacterial substance (s) may be released in the stomach. The enteric coating layered pellets may further be covered with an overcoating layer before being formulated into the tablet and they may also contain one or more separating layer(s) optionally containing alkaline substance(s).

Process

The process for the manufacture of the dosage form represents a further aspect of the invention. After formulation of the pellets by spray coating or layering of the proton pump inhibitor onto seeds, or by extrusion/spheronization or granulation, e.g. rotor granulation of homogeneous pellets, the pellets are first optionally covered with the separating layer(s) and then with the enteric coating layer(s) or a separating layer is spontaneously developed in situ between an alkaline core material and the enteric coating layer material. The coating is carried out as described above and in the accompanying examples. The preparation of the granulation comprising the antibacterial compound(s) is also described above and in the examples. The pharmaceutical processes can preferably be completely water-based.

The enteric coating layered pellets, with or without an over-coat, are mixed with the prepared granules, tablet excipients and other pharmaceutical acceptable additives and compressed into tablets. The tablet may be in the form of a two layer tablet, wherein one layer comprises the enteric coating layered pellets optionally mixed with inactive excipients and the other layer comprises the prepared granules of the antibacterial substance(s). Alternatively, the different active substances in the form of powders may be intimately dry mixed with tablet excipients, wet massed and compressed into conventional tablets before applying an optional separating layer and an enteric coating layer. The tablet may be in the form of a two layer enteric coating layered tablet, wherein one layer comprises one of the active substances and the other layer comprises the other active substance(s). As a further alternative, the proton pump inhibitor in the form of enteric coating layered pellets may be filled in a capsule together with the antibacterial substance(s) in the form of a granulation optionally mixed with pharmaceutical excipients.

Use of the Preparation

The dosage forms according to the invention are especially advantageous in the treatment of *H. pylori* infections. They are administered one to several times a day, preferably once or twice daily. The typical daily dose of the active substances varies and will depend on various factors such as the individual requirements of the patients, the mode of administration and disease. In general each dosage form will comprise 0.1–200 mg of the proton pump inhibitor and 0.1 mg–1.2 g of the antibacterial compound(s). Preferably, each dosage form will comprise 10–80 mg of the proton pump inhibitor and 100–900 mg of the antibacterial compound(s), and more preferably 20–40 mg of proton pump inhibitor and 250–650 mg of the antibacterial compound(s), respectively.

The multiple unit tablet preparation is also suitable for dispersion in an aqueous liquid with neutral or slightly acidic pH-value before being orally administered or fed through a nasogastric tube.

The invention is illustrated more in detail in the following examples.

EXAMPLES

Example 1

Multiple unit dosage form comprising omeprazole and metronidazole (batch size 10.000 tablets).

| Core material | |
|---|---|
| Magnesium omeprazole | 12.00 kg |
| Sugar sphere seeds | 12.00 kg |
| Hydroxypropyl methylcellulose | 1.8 kg |
| Water purified | 35.4 kg |
| Separating layer | |
| Core material (acc. to above) | 23.50 kg |
| Hydroxypropyl cellulose | 2.35 kg |
| Talc | 4.03 kg |
| Magnesium stearate | 0.34 kg |
| Water purified | 48.00 kg |
| Enteric coating layer | |
| Pellets covered with separating layer (acc. to above) | 29.00 kg |
| Methacrylic acid copolymer (30% suspension) | 38.70 kg |
| Triethyl citrate | 3.48 kg |
| Mono- and diglycerides (NF) | 0.58 kg |
| Polysorbate 80 | 0.06 kg |
| Water purified | 22.68 kg |
| Over-coating layer | |
| Enteric coating layered pellets (acc. to above) | 44.7 kg |
| Hydroxypropyl methylcellulose | 0.58 kg |
| Water purified | 11.6 kg |
| Tablets | |
| Prepared pellets comprising omeprazole as prepared above | 933 g |
| Metronidazole | 4000 g |
| Sodium starch glycolate | 500 g |
| Aerosil ® | 25 g |
| Sodium lauryl sulphate | 20 g |
| Polyvidone K90 | 253.1 g |
| Microcrystalline cellulose | 1181 g |
| Water purified | 2278 g |
| Sodium stearyl fumarate | 66.5 g |
| Tablet coating solution (for 10 kg tablets) | |
| Hydroxypropyl methylcellulose | 250 g |
| Polyethylene glycol 6000 | 62.5 g |
| Titanium dioxide | 62.5 g |
| Water purified | 2125 g |
| Hydrogen pyroxide | 0.75 g |

Suspension layering is performed in a fluid bed apparatus. Magnesium omeprazole is sprayed onto sugar sphere seeds from a water suspension containing the dissolved binder. The size of sugar sphere seeds are in the range of 0.25 to 0.35 mm.

The prepared core material is covered with a separating layer in a fluid bed apparatus with a hydroxypropyl cellulose solution containing talc and magnesium stearate. The enteric coating layer consisting of methacrylic acid copolymer, mono- and diglycerides, triethyl citrate and polysorbate is sprayed onto the pellets covered with a separating layer in a fluid bed apparatus. In a fluid bed apparatus enteric coating layered pellets are coated with hydroxypropyl methylcellulose solution. The over-coating layered pellets are classified by sieving.

Sodium lauryl sulphate and polyvidone K90 are dissolved in purified water to form the granulation liquid. Metronidazole, sodium starch glycolate and Aerosil® are dry-mixed. The granulating liquid is added to the powder mixture and the mass is wet-mixed. The wet mass is dried in a steamoven at 50° C. The prepared granulation is milled through sieve 1 mm in an oscillating mill equipment.

The enteric coating layered pellets with an over-coating layer, prepared granules, microcrystalline cellulose and sodium stearyl fumarate are mixed and compressed into tablets using a rotary tableting machine equipped with 8.5×17 mm oval punches. The amount of omeprazole in each tablet is approx. 20 mg and the amount of metronidazole is approx. 400 mg. Tableting speed is set to 50 rpm and the upper punch force is set to 20 kN. Tablet hardness measured is 150–164N.

The obtained tablets are covered with a conventional tablet coating layer.

Example 2

Multiple unit dosage form comprising omeprazole and clarithromycin (batch size 10.000 tablets).

| Tablets | |
|---|---|
| Enteric coating layered pellets with an over-coating layer (manufacturing and composition as in example 1) | 978 g |
| Clarithromycin | 2500 g |
| Microcrystalline cellulose | 3000 g |
| Sodium starch glycolate | 350 g |
| Aerosil ® | 40 g |
| Sodium lauryl sulphate | 12.5 g |
| Polyvidone K90 | 384.8 g |
| Water purified | 3463 g |
| Magnesium stearate | 105 g |
| Tablet coating solution (for 10 kg tablets) | |
| Hydroxypropyl methylcellulose | 250 g |
| Polyethylene glycol 6000 | 62.5 g |
| Titanium dioxide | 62.5 g |
| Water purified | 2125 g |
| Hydrogen pyroxide | 0.75 g |

Sodium lauryl sulphate and polyvidone K90 are dissolved in purified water to form the granulation liquid. Clarithromycin, microcrystalline cellulose, sodium starch glycolate and Aerosil® are dry-mixed. The granulating liquid is added to the powder mixture and the mass is wet-mixed. The wet mass is dried in a steam-oven. The prepared granulation is milled through sieve 1 mm in an oscillating mill equipment.

The enteric coating layered pellets with an over-coating layer, prepared granules and magnesium stearate are mixed and compressed into tablets as in example 1. The amount of omeprazole in each tablet is approx. 20 mg and the amount of clarithromycin is approx. 250 mg. Tableting speed is set to 50 rpm and the upper punch force is set to 14 kN. Tablet hardness measured is 178–189N.

The obtained tablets are covered with a conventional tablet coating layer.

Example 3

Multiple unit dosage form comprising omeprazole and clarithromycin (batch size 10.000 tablets).

| Tablets | |
|---|---|
| Enteric coating layered pellets with an over-coating layer (manufacturing and composition as in example 1) | 978 g |
| Clarithromycin | 5000 g |
| Microcrystalline cellulose | 2500 g |
| Sodium starch glycolate | 350 g |
| Aerosil ® | 40 g |
| Sodium lauryl sulphate | 25 g |
| Polyvidone K90 | 361.9 g |
| Water purified | 3257 g |
| Magnesium stearate | 91.7 g |
| Tablet coating solution (for 10 kg tablets) | |
| Hydroxypropyl methylcellulose | 250 g |
| Polyethylene glycol 6000 | 62.5 g |
| Titanium dioxide | 62.5 g |
| Water purified | 2125 g |
| Hydrogen pyroxide | 0.75 g |

The antibacterial granulation is manufactured as in example 2. Enteric coating layered pellets with an over-coating layer, prepared granules and magnesium stearate are mixed and compressed into tablets using a rotary tableting machine equipped with 10×21 mm oval punches. The amount of omeprazole in each tablet is approx. 20 mg and the amount of clarithromycin is approx. 500 mg. Tableting speed is set to 50 rpm and the upper punch force is set to 20 kN. Tablet hardness measured is 105–128N.

The obtained tablets are covered with a conventional tablet coating layer.

Example 4

Multiple unit dosage form comprising, metronidazole and clarithromycin (batch size 2.500 tablets).

| Core material | |
|---|---|
| Magnesium omeprazole | 15.00 kg |
| Sugar sphere seeds | 15.00 kg |
| Hydroxypropyl methylcellulose | 2.25 kg |
| Water purified | 40.25 kg |
| Separating layer | |
| Core material (acc. to above) | 15.00 kg |
| Hydroxypropyl cellulose | 1.5 kg |
| Talc | 2.57 kg |
| Magnesium stearate | 0.21 kg |
| Water purified | 30.00 kg |
| Enteric coating layer | |
| Pellets covered with separating layer (acc. to above) | 18.00 kg |
| Methacrylic acid copolymer (30% suspension) | 30.00 kg |
| Triethyl citrate | 2.7 kg |
| Mono- and diglycerides (NF) | 0.49 kg |
| Polysorbate 80 | 0.05 kg |
| Water purified | 19.00 kg |

-continued

| Tablets | |
|---|---|
| Enteric coating layered pellets (acc. to above) | 246 g |
| Clarithromycin | 625 g |
| Metronidazole | 1000 g |
| Microcrystalline cellulose | 375 g |
| Sodium starch glycolate | 125 g |
| Aerosil ® | 10 g |
| Sodium lauryl sulphate | 8 g |
| Polyvidone K90 | 117.8 g |
| Water purified | 1060 g |
| Sodium stearyl fumarate | 48.2 g |

Suspension layering is performed in a fluid bed apparatus. Magnesium omeprazole is sprayed onto sugar sphere seeds from a water suspension containing the dissolved binder.

The prepared core material is covered with a separating layer in a fluid bed apparatus with a hydroxypropyl cellulose solution containing talc and magnesium stearate. The enteric coating layer consisting of methacrylic acid copolymer, mono- and diglycerides, triethyl citrate and polysorbate is sprayed onto the pellets covered with a separating layer in a fluid bed apparatus. The enteric coating layered pellets are classified by sieving.

Sodium lauryl sulphate and polyvidone K90 are dissolved in purified water to form the granulation liquid. Clarithromycin, metronidazole, microcrystalline cellulose, sodium starch glycolate and Aerosil are dry-mixed. The granulating liquid is added to the powder mixture and the mass is wet-mixed. The wet mass is dried in a steam-oven. The prepared granulation is milled through sieve 1 mm in an oscillating mill equipment.

Enteric coating layered pellets, prepared granules and sodium stearyl fumarate are mixed and compressed into tablets as in example 3. The amount of omeprazole in each tablet is approx. 20 mg, the amount of metronidazole is 400 mg and the amount of clarithromycin is 250 mg. Tableting speed is set to 50 rpm and the upper punch force is set to 24 kN. Tablet hardness measured is 130–142N.

Example 5

Multiple unit dosage form comprising lansoprazole and clarithromycin (batch size 1.000 tablets).

| Core material | |
|---|---|
| Lansoprazole | 400 g |
| Sugar sphere seeds | 400 g |
| Hydroxypropyl methylcellulose | 80 g |
| Water purified | 1200 g |
| Separating layer | |
| Core material (acc. to above) | 400 g |
| Hydroxypropyl cellulose | 40 g |
| Talc | 69 g |
| Magnesium stearate | 6 g |
| Water purified | 800 g |
| Enteric coating layer | |
| Pellets covered with a separating layer (acc. to above) | 400 g |
| Methacrylic acid copolymer (30% suspension) | 667 g |
| Triethyl citrate | 60 g |
| Mono- and diglycerides (NF) | 10 g |

| -continued | |
|---|---|
| Polysorbate 80 | 1 g |
| Water purified | 391 g |
| Tablets | |
| Enteric coating layered pellets (acc. to above) | 89.8 g |
| Clarithromycin | 250 g |
| Microcrystalline cellulose | 300 g |
| Sodium starch glycolate | 35 g |
| Aerosil ® | 4 g |
| Sodium lauryl sulphate | 1.25 g |
| Polyvidone K90 | 45.2 g |
| Water purified | 406.8 g |
| Magnesium stearate | 10.1 g |

Suspension layering is performed in a fluid bed apparatus. Lansoprazole is sprayed onto the sugar sphere seeds from a suspension containing the dissolved binder in a water solution. Pellets covered with separating layer and enteric coating layer are produced as in example 1. The antibacterial granulation is manufactured as in example 2.

Enteric coating layered pellets, prepared granules and magnesium stearate are mixed and compressed into tablets using a rotary tableting machine equipped with 8.5×17 mm oval punches. The amount of lansoprazole in each tablet is approx. 20 mg and the amount of clarithromycin is approx. 250 mg. The upper punch force is set to 5.8 kN, and the tablet hardness is measured 63N.

Example 6

Multiple unit dosage form comprising (s)-omeprazole magnesium salt, metronidazole and clarithromycin (batch size 200 tablets).

| Core material | |
|---|---|
| (s)-Omeprazole magnesium salt | 120 g |
| Sugar sphere seeds | 150 g |
| Hydroxypropyl methylcellulose | 18 g |
| Polysorbate 80 | 2.4 g |
| Water purified | 562 g |
| Separating layer | |
| Core material (acc. to above) | 200 g |
| Hydroxypropyl cellulose | 30 g |
| Talc | 51.4 g |
| Magnesium stearate | 4.3 g |
| Water purified | 600 g |
| Enteric coating layer | |
| Pellets covered with separating layer (acc. to above) | 250 g |
| Methacrylic acid copolymer (30% suspension) | 333.7 g |
| Triethyl citrate | 30 g |
| Mono- and diglycerides (NF) | 5 g |
| Polysorbate 80 | 0.5 g |
| Water purified | 196 g |
| Metronidazole and clarithromycin granulation | |
| Clarithromycin | 3500 g |
| Metronidazole | 5600 g |
| Microcrystalline cellulose | 1400 g |
| Sodium starch glycolate | 700 g |
| Aerosil ® | 56 g |
| Polyvidon K90 | 511 g |
| Water purified | 4600 g |

| -continued | |
|---|---|
| Tablets | |
| Pellets comprising (s)-omeprazole Mg-salt (acc. to above) | 25.5 g |
| Granulation comprising clarithromycin and metronidazole (acc. to above) | 168.1 g |
| Microcrystalline cellulose | 40 g |
| Sodium stearyl fumarate | 4.7 g |
| Tablet coating solution (for 10 kg tablets) | |
| Hydroxypropyl methylcellulose | 250 g |
| Polyethylene glycol 6000 | 62.5 g |
| Titanium dioxide | 62.5 g |
| Water purified | 2125 g |
| Hydrogen pyroxide | 0.75 g |

Suspension layering is performed in a fluid bed apparatus. (s)-Omeprazole magnesium salt is sprayed onto sugar sphere seedes from a water suspension containing the dissolved binder and polysorbate 80. The size of sugar sphere seedes are in the range of 0.25 to 0.35 mm.

The prepared core material is covered with a separating layer in a fluid bed apparatus with hydroxypropyl cellulose solution containing talc and magnesium stearate. The enteric coating layer consisting of methacrylic acid copolymer, mono-and diglycerides, triethyl citrate and polysorbate is sprayed onto the pellets covered with a separating layer in a fluid bed apparatus. The enteric coating layered pellets are classified by sieving.

Polyvidone K90 is dissolved in purified water to form the granulation liquid. Clarithromycin, metronidazole, microcrystalline cellulose, sodium starch glycolate and Aerosil® are dry-mixed. The granulating liquid is added to the powder mixture and the mass is wet-mixed. The wet mass is dried in a steam-oven. The prepared granulation is milled through sieve 1 mm in an oscillating mill equipment.

The enteric coating layered pellets, prepared granules, microcrystalline cellulose and magnesium stearate are mixed and compressed into tablets on a tableting machine equipped with 10×21 mm oval punches. The amount of (s)-omeprazole is approx. 20 mg, the amount of metronidazole is approx. 400 mg and the amount of clarithromycin is approx. 250 mg. Tablet hardness tested with a Schleuniger apparatus was 140–150N.

The obtained tablets are covered with a conventional tablet coating layer.

The results from tests on acid resistance of the compressed tablets are disclosed in Table 1, below.

TABLE 1

| Example No | Acid resistance, tablets (%), n = 3 |
|---|---|
| 1 | 95 |
| 2 | 99 |
| 3 | 91 |
| 4 | 92 |
| 5 | 90 |
| 6 | 93 |

Example 7

An enteric coating layered tablet comprising magnesium omeprazole, clarithromycin and metronidazol (batch size 1.000 tablets).

| Tablets | |
|---|---|
| Magnesium omeprazole | 20 g |
| Clarithromycin | 250 g |
| Metronidazole | 400 g |
| Microcrystalline cellulose | 150 g |
| Sodium starch glycolate | 50 g |
| Aerosil ® | 4 g |
| Sodium lauryl sulphate | 3.2 g |
| Polyvidone K90 | 50 g |
| Water purified | 450 g |
| Sodium stearyl fumarate | 18 g |
| Solution for separating layer (for 10 kg tablets) | |
| Hydroxypropyl methylcellulose | 300 g |
| Hydrogen peroxide (30%) | 0.003 g |
| Water purified | 2700 g |
| Solution for enteric coating layer (for 10 kg tablets) | |
| Methacrylic acid copolymer dispersion (30%) | 2450 g |
| Polyethylene glycol 400 | 80 g |
| Titanium dioxide | 100 g |
| Water purified | 1960 g |

Sodium lauryl sulphate and polyvidone K90 are dissolved in purified water to form the granulation liquid. Magnesium omeprazole, clarithromycin, metronidazole, microcrystalline cellulose, sodium starch glycolate and Aerosil® are dry-mixed. The granulating liquid is added to the powder mixture and the mass is wet-mixed. The wet mass is dried in a steam-oven. The prepared granulation is milled through sieve 1 mm in an oscillating mill equipment.

The prepared granules and sodium stearyl fumarate are mixed and compressed into tablets using a rotary tableting machine equipped with 8.5×19 mm oval punches. The amount of omeprazole in each tablet is 20 mg, the amount of clarithromycin is 250 mg and the amount of metronidazole is 400 mg.

The obtained tablets are covered with a separating layer and an enteric tablet coating layer.

Example 8

An enteric coating layered tablet comprising lansoprazole and clarithromycin (batch size 1.000 tablets).

| Tablets | |
|---|---|
| Lansoprazole | 20 g |
| Clarithromycin | 250 g |
| Microcrystalline cellulose | 150 g |
| Sodium starch glycolate | 50 g |
| Aerosil ® | 4 g |
| Sodium lauryl sulphate | 3.2 g |
| Polyvidone K90 | 50 g |
| Water purified | 450 g |
| Sodium stearyl fumarate | 18 g |
| Solution for separating layer (for 10 kg tablets) | |
| Hydroxypropyl methylcellulose | 300 g |
| Hydrogen peroxide (30%) | 0.003 g |
| Water purified | 2700 g |
| Solution for enteric coating layer (for 10 kg tablets) | |
| Methacrylic acid copolymer dispersion (30%) | 2450 g |
| Polyethylene glycol 400 | 80 g |
| Titanium dioxide | 100 g |
| Water purified | 1960 g |

Sodium lauryl sulphate and polyvidone K90 are dissolved in purified water to form the granulation liquid. Lansoprazole, clarithromycin, microcrystalline cellulose, sodium starch glycolate and Aerosile® are dry-mixed. The granulation liquid is added to the powder mixture and the mass is wet-mixed. The wet mass is dried in a steam-oven. The prepared granulation is milled through sieve 1 mm in an oscillating mill equipment.

The prepared granules and sodium stearyl fumarate are mixed and compressed into tablets using a rotary tableting machine equipped with 8.5×19 mm oval punches. The amount of lansoprazole in each tablet is 20 mg, the amount of clarithromycin is 250 mg.

The obtained tablets are covered with a separating layer and an enteric tablet coating layer.

Example 9

A capsule formulation comprising omeprazole and metronidazol.

| Core material | |
|---|---|
| Magnesium omeprazole | 10.00 kg |
| Sugar sphere seeds | 10.00 kg |
| Hydroxypropyl methylcellulose | 1.5 kg |
| Water purified | 29.65 kg |
| Separating layer | |
| Core material (acc. to above) | 20.00 kg |
| Hydroxypropyl cellulose | 2.00 kg |
| Talc | 3.43 kg |
| Magnesium stearate | 0.29 kg |
| Water purified | 40.00 kg |
| Enteric coating layer | |
| Pellets covered with a separating layer (acc. to above) | 24.00 kg |
| Methacrylic acid copolymer (30% suspension) | 40.00 kg |
| Triethyl citrate | 3.6 kg |
| Mono- and diglycerides (NF) | 0.6 kg |
| Polysorbate 80 | 0.06 kg |
| Water purified | 24.45 kg |
| Metronidazole granulation | |
| Metronidazole | 5000 g |
| Polyvidone K90 | 62.6 g |
| Water purified | 562.9 g |

Polyvidon K90 is dissolved in purified water to form the granulation liquid. The liquid is added to metronidazole and the mass is wet-mixed. The wet mass is dried in a steam oven. The prepared granulation is milled through sieve 1 mm in an oscillating mill equipment.

| Capsules | |
|---|---|
| Metronidazole granulation (acc. to above) | 1250.8 g |

-continued

| | |
|---|---|
| Enteric coating layered pellets (acc. to above) (manufacturing as in Example 4) | 104 mg/capsule |
| Magnesium stearate | 24.8 g |

The metronidazole granulation is mixed with magnesium stearate. Prepared granules and enteric coating layered pellets are filled into capsules, size 0, using a capsule filling machine equipped with powder dosing unit and pellet filler. The amount of omeprazole in each capsule is 20 mg and the amount of metronidazole is 400 mg. Capsule filling speed is set to 61 rpm.

Example 10

A capsule formulation comprising omeprazole and clarithromycin.

| | |
|---|---|
| Core material | |
| Magnesium omeprazole | 15.00 kg |
| Sugar sphere seeds | 15.00 kg |
| Hydroxypropyl methylcellulose | 2.25 kg |
| Water purified | 44.00 kg |
| Separating layer | |
| Core material (acc. to above) | 30.00 kg |
| Hydroxypropyl cellulose | 3.00 kg |
| Talc | 5.14 kg |
| Magnesium stearate | 0.43 kg |
| Water purified | 60.00 kg |
| Enteric coating layer | |
| Pellets covered with a separating layer (acc. to above) | 750 g |
| Methacrylic acid copolymer | 322.5 g |
| Triethyl citrate | 96.8 g |
| Mono- and diglycerides (NF) | 16.1 g |
| Polysorbate 80 | 1.61 g |
| Water purified | 631.4 g |
| Over-coating layer | |
| Hydroxypropyl methylcellulose | 22.5 g |
| Water purified | 427.5 g |
| Clarithromycin granulation | |
| Clarithromycin | 5000 g |
| Ethanol (99.5%) | 2064 g |
| Sodium lauryl sulphate | 50 g |

Sodium lauryl sulphate is dissolved in ethanol to form the granulation liquid. The liquid is added to clarithromycin and the mass is wet-mixed. The wet mass is dried in a steam oven. The prepared granulation is milled through sieve 1 mm in an oscillating mill equipment.

| | |
|---|---|
| Capsules | |
| Clarithromycin granulation (acc. to above) | 1500 g |
| Hydroxypropyl cellulose (L-HPC) | 75 g |
| Magnesium stearate | 31.5 g |
| Pellets covered with an overcoating layer (acc. to above and manufacturing as in example 1) | 96.7 mg/capsule |

The clarithromycin granulation is mixed with L-HPC and magnesium stearate and capsules of size 00 is filled as in example 8. The amount of omeprazole in each capsule is 20 mg and the amount of clarithromycin is 500 mg.

Example 11

A capsule formulation comprising omeprazole, clarithromycin and metronidazole.

| | |
|---|---|
| Capsules | |
| Clarithromycin granulation (manufacturing and composition as in example 9) | 1805 g |
| Hydroxypropyl cellulose (L-HPC) | 90.3 g |
| Metronidazole | 2670 g |
| Magnesium stearate | 91.3 g |
| Pellets covered with an overcoating layer (manufacturing and composition as example 1) | 96.7 mg/capsule |

The clarithromycin granulation is mixed with metronidazole, L-HPC and magnesium stearate. Capsules of size 00 is filled as in example 8. The amount of omeprazole in each capsule is 20 mg, the amount of metronidazole is 400 mg and the amount of clarithromycin is 250 mg.

Example 12

A dosage form comprising lansoprazole and clarithromycin, filled into capsules in the form of granules.

| | |
|---|---|
| Core material | |
| Lansoprazole | 400 g |
| Sugar sphere seeds | 400 g |
| Hydroxypropyl methylcellulose | 80 g |
| Water purified | 1200 g |
| Separating layer | |
| Core material (acc. to above) | 400 g |
| Hydroxypropyl cellulose | 40 g |
| Talc | 69 g |
| Magnesium stearate | 6 g |
| Water purified | 800 g |
| Enteric coating layer | |
| Pellets covered with separating layer (acc. to above) | 400 g |
| Methacrylic acid copolymer (30% suspension) | 667 g |
| Triethyl citrate | 60 g |
| Mono- and diglycerides (NF) | 10 g |
| Polysorbate 80 | 1 g |
| Water purified | 391 g |
| Clarithromycin granulation | |
| Clarithromycin | 5000 g |
| Ethanol (99.5%) | 2064 g |
| Sodium lauryl sulphate | 50 g |

Soidum lauryl sulphate is dissolved in ethanol to form the granulation liquid. The liquid is added to clarithromycin and the mass is wet-mixed. The wet mass is dried in a steam oven. The prepared granulation is milled through sieve 1 mm in an oscillating mill equipment.

| | |
|---|---|
| Capsules | |
| Clarithromycin granulation (acc. to above) | 1500 g |

| | |
|---|---|
| Hydroxypropyl cellulose (L-HPC) | 75 g |
| Magnesium stearate | 31.5 g |
| Enteric coating layered pellets (acc. to above and manufacturing as in example 5) | 94 mg/capsule |

The clarithromycin granulation is mixed with L-HPC and magnesium stearate and capsules of size 00 is filled as in example 8. The amount of lansoprazole in each capsule is 20 mg and the amount of clarithromycin is 500 mg.

The best mode to carry out the invention are dosage forms of the compositions described in Examples 3, 4 and 6.

The enteric coating layered pellets and other intermediate products used in the compositions described above, may also be prepared as described in the following examples.

Example 13

Preparation of enteric coating layered pellets by extrusion/spheronization.

| | |
|---|---|
| Core material | |
| Magnesium omeprazole | 600 g |
| Mannitol | 1000 g |
| Microcrystalline cellulose | 300 g |
| Hydroxypropyl cellulose | 100 g |
| Sodium lauryl sulphate | 6 g |
| Water purified | 802 g |
| Separating layer | |
| Core material (acc. to above) | 400 g |
| Hydroxypropyl methylcellulose | 48 g |
| Water purified | 960 g |
| Enteric coating layer | |
| Pellets covered with separating layer (acc. to above) | 200 g |
| Methacrylic acid copolymer | 100 g |
| Triethyl citrate | 30 g |
| Mono- and diglycerides (NF) | 5 g |
| Polysorbate 80 | 0.5 g |
| Water purified | 309 g |

Sodium lauryl sulphate is dissolved in purified water to form the granulation liquid. Magnesium omeprazole, mannitol, microcrystalline cellulose and hydroxypropyl cellulose are dry-mixed. The granulation liquid is added to the powder mixture and the mass is wet-mixed.

The wet mass is forced through an extruder equipped with screens of size 0.5 mm. The extrudate is spheronized on a friction plate in a spheronizing apparatus. The core material is dried in a fluid bed dryer and classified. The prepared core material is covered by a separating layer in a fluid bed apparatus with a hydroxypropyl methylcellulose/water solution.

The enteric coating layer is applied to the pellets covered with separating layer from an aqueous dispersion of methacrylic acid copolymer plasticized with triethyl citrate to which a mono- and diglycerides/polysorbate dispersion has been added. The pellets are dried in a fluid bed apparatus.

Example 14

Preparation of enteric coating layered pellets by powder.

| | |
|---|---|
| Core material | |
| Magnesium omeprazole | 1500 g |
| Sugar sphere seeds | 1500 g |
| Hydroxypropyl methylcellulose | 420 g |
| Aerosil ® | 8 g |
| Water purified | 4230 g |
| Separating layer | |
| Core material (acc. to above) | 500 g |
| Hydroxypropyl cellulose | 40 g |
| Talc | 67 g |
| Magnesium stearate | 6 g |
| Water purified | 800 g |
| Enteric coating layer | |
| Pellets covered with separating layer (acc. to above) | 500 g |
| Methacrylic acid copolymer | 200 g |
| Triethyl citrate | 60 g |
| Water purified | 392 g |

Magnesium omeprazole, part of the hydroxypropyl methylcellulose and Aerosil® are dry-mixed forming a powder. Sugar sphere seeds (0.25–0.40 mm) are layered with the powder in a centrifugal fluidized coating granulator while spraying a hydroxypropyl methylcellulose solution (6%, w/w).

The prepared core material is dried and covered by a separating layer in a centrifugal fluidized coating-granulator. A fluid bed apparatus is used for enteric coating layereing.

Example 15

Preparation of enteric coating layered pellets with silicon dioxide seeds.

| | |
|---|---|
| Core material | |
| Magnesium omeprazole | 8.00 kg |
| Silicon dioxide | 8.00 kg |
| Hydroxypropyl methylcellulose | 1.41 kg |
| Sodium lauryl sulphate | 0.08 kg |
| Water purified | 28.00 kg |
| Separating layer | |
| Core material (acc. to above) | 10.00 kg |
| Hydroxypropyl methylcellulose | 0.80 kg |
| Water purified | 10.00 kg |
| Enteric coating layer | |
| Pellets covered with separating layer (acc. to above) | 300 g |
| Methacrylic acid copolymer | 124 g |
| Polyethylene glycol 400 | 25 g |
| Mono- and diglycerides (NF) | 3 g |
| Polysorbate 80 | 1 g |
| Water purified | 463 g |

Suspension layering is performed in a fluid bed apparatus. Magnesium omeprazole is sprayed onto the silicon dioxide seeds from a water suspension containing the dissolved binder and a surface active ingredient.

The prepared core material is covered with a separating layer in a fluid bed apparatus with a hydroxypropyl methylcellulose solution. The enteric coating layer consisting of methacrylic acid copolymer, mono- and diglycerides, polyethylene glycol 400 and polysorbate is sprayed onto the pellets covered with separating layer in a fluid bed apparatus.

Example 16

Preparation of enteric coating layered pellets.

| Enteric coating layer | |
| --- | --- |
| Pellets covered with separating layer (manufacturing and composition as in example 13) | 500 g |
| Methacrylic acid copolymer | 250 g |
| Polyethylene glycol 6000 | 75 g |
| Mono- and diglycerides (NF) | 12.5 g |
| Polysorbate 80 | 1.2 g |
| Water purified | 490 g |

Example 17

Preparation of enteric coating layered pellets.

| Enteric coating | |
| --- | --- |
| Pellets covered with separating layer (manufacturing and composition as in example 1) | 500 g |
| Hydroxypropyl methylcellulose phthalate | 250 g |
| Cetanol | 50 g |
| Ethanol (95%) | 1000 g |

Example 18

Preparation of enteric coating layered pellets.

| Core material | |
| --- | --- |
| Omeprazole | 225 g |
| Mannitol | 1425 g |
| Hydroxypropyl cellulose | 60 g |
| Microcrystalline cellulose | 40 g |
| Lactose anhydrous | 80 g |
| Sodium lauryl sulphate | 5 g |
| Disodium hydrogen phosphate dihydrate | 8 g |
| Water purified | 350 g |
| Separating layer | |
| Core material (acc. to above) | 300 g |
| Hydroxypropyl cellulose | 30 g |
| Talc | 51 g |
| Magnesium stearate | 4 g |
| Enteric coating layer | |
| Pellets covered with separating layer (acc. to above) | 300 g |
| Methacrylic acid copolymer | 140 g |
| Triethyl citrate | 42 g |
| Mono- and diglycerides (NF) | 7 g |
| Polysorbate 80 | 0.7 g |

The dry ingredients for producing the core material are well mixed in a mixer. Addition of granulation liquid is made and the mixture is kneaded and granulated to a proper consistency. The wet mass is pressed through an extruder screen and the granules are converted into a spherical form in a spheronizer. The core material is dried in a fluid bed apparatus and classified into a suitable particle size range, e.g. 0.5–1.0 mm. The prepared core material is covered with a separating layer and enteric coating layered as described in previous examples.

Preparation of active substance.

Magnesium omeprazole used in the examples is produced according to the process described in WO/SE94/00680, omeprazole is produced according to the process disclosed in EP-A 1 0005129, and the single enantiomers of omeprazole salts are produced as described in WO/SE94/00509. These documents are hereby incorporated in a whole by reference.

What is claimed is:

1. An oral pharmaceutical composition consisting essentially of, as a first component, at least one antibacterial compound, and as a second component, an acid susceptible proton pump inhibitor, wherein: (a) the composition is in the form of a multiple unit tablet; (b) the proton pump inhibitor is in the form of pellets covered with an enteric coating polymer layer; (c) the first component is separated from the proton pump inhibitor by the enteric coating layer covering the second component; and (d) the enteric coating layer has mechanical properties such that the acid resistance of the enteric coated pellets is not significantly affected by compression of the pellets with the other tablet components during tableting.

2. The composition of claim 1, wherein a pharmaceutically acceptable tablet excipient is included.

3. The composition of claim 1, wherein the antibacterial component is two different antibiotic compounds with different activities.

4. The composition according to claim 1, wherein the antibacterial component in the form of granules of the antibacterial component.

5. The composition of claim 1, wherein the proton pump inhibitor is omeprazole or a pharmaceutically acceptable salt of omeprazole.

6. The composition of claim 1, wherein the proton pump inhibitor is omeprazole, an alkaline salt of omeprazole, a (−)-enantiomer of omeprazole or an alkaline salt of the (−)-enantiomer of omeprazole.

7. The composition of claim 1, wherein the proton pump inhibitor is S-omeprazole magnesium salt.

8. The composition of claim 1, wherein the proton pump inhibitor is lansoprazole, a pharmaceutically acceptable salt of lansoprazole, a single enantiomer of lansoprazole or a pharmaceutically acceptable salt of the enantiomer of lansoprazole.

9. The composition of claim 1, wherein the antibacterial component is clarithromycin, metronidazole or a combination thereof.

10. The composition of claim 1, wherein the antibacterial component is selected from the group consisting of amoxycillin, clarithromycin, metronidazole and a combination thereof.

11. The composition of claim 1, wherein the amount of the antibacterial component is in the range of 100–900 mg and the amount of the proton pump inhibitor is in the range of 10–80 mg.

12. The composition of claim 1, wherein the amount of the first antibacterial component is in the range of 250–650 mg and the amount of the proton pump inhibitor is in the range of 20–40 mg.

13. The composition of claim 1, wherein the tablet is in the form of two separate layers.

14. The composition of claim 13, wherein the acid susceptible proton pump inhibitor is located in one layer and wherein the antibacterial component is located in the other layer.

15. The composition of claim 1, wherein the acid resistance of the enteric coating layered pellets is in compliance with the requirements on enteric coating layered articles as defined in the United States Pharmacopeia and does not decrease more than 10% upon tableting of the pellets into the multiple unit dosage tablet.

16. The composition of claim 1, wherein the proton pump inhibitor is covered by a separating layer located underneath the enteric coating layer.

17. The composition of claim 1, wherein the enteric coating layer of the pellet comprises more than one layer.

18. The composition of claim 1, wherein the enteric coating layer of the pellet comprises a plasticized enteric coating layer material.

19. The composition of claim 1, wherein the enteric coating layered pellets are further covered with an overcoating layer comprising a pharmaceutically acceptable excipient.

20. The composition of claim 1, wherein the multiple unit dosage tablet is divisible.

21. A method for the treatment of disorders associated with *Helicobacter pylori* infection in mammals and man comprising administering to a host in need thereof a therapeutically effective dose of a composition according to claim 1.

22. The composition of claim 20, wherein the tablet is dispersible to a suspension of individually enteric coating layered pellets in an aqueous liquid.

23. The composition of claim 18, wherein the amount of plasticizer is 20–50% by weight of the enteric coating layer polymer.

24. A process for the manufacture of an oral pharmaceutical composition in the form of a multiple unit dosage tablet consisting essentially of, as a first component, at least one antibacterial compound, and as a second component, an acid susceptible proton pump inhibitor, wherein the process comprises the steps of:

(a) preparing the proton pump inhibitor in the form of enteric coating layered pellets;

(b) mixing the enteric coated pellets with a prepared granules of the antibacterial component;

(c) drying the mixture; and (d) compressing the mixture into a multiple unit tablet without affecting any significant change of the acid resistance of the enteric coating layered pellets.

25. The process according to claim 24, further comprising the step of admixing a pharmaceutically acceptable excipient to the tablet mixture.

* * * * *